(12) United States Patent
Yeom et al.

(10) Patent No.: US 8,557,795 B2
(45) Date of Patent: Oct. 15, 2013

(54) **COMPOSITION CONTAINING *CHAMAECYPARIS OBTUSA* POLYSACCHARIDES TO BE EXTERNALLY APPLIED TO THE SKIN**

(75) Inventors: Myeong Hun Yeom, Yongin-si (KR); Won Seok Park, Seoul (KR); Duck Hee Kim, Seoul (KR); Han Kon Kim, Suwon-si (KR); Jeong Ok Kim, Jinju-si (KR)

(73) Assignee: Amorepacific Corporation, Seoul (KR)

( * ) Notice: Subject to any disclaimer, the term of this patent is extended or adjusted under 35 U.S.C. 154(b) by 14 days.

(21) Appl. No.: 13/319,765

(22) PCT Filed: May 27, 2010

(86) PCT No.: PCT/KR2010/003348
§ 371 (c)(1),
(2), (4) Date: Nov. 10, 2011

(87) PCT Pub. No.: WO2010/137882
PCT Pub. Date: Dec. 2, 2010

(65) Prior Publication Data
US 2012/0065159 A1    Mar. 15, 2012

(30) Foreign Application Priority Data

May 29, 2009   (KR) ........................ 10-2009-0047317

(51) Int. Cl.
*A61K 8/73* (2006.01)
(52) U.S. Cl.
USPC .......................................................... 514/54
(58) Field of Classification Search
USPC .......................................................... 514/54
See application file for complete search history.

(56) References Cited

FOREIGN PATENT DOCUMENTS

| KR | 10-2007-0102911 | 10/2007 |
|---|---|---|
| KR | 10-2009-0038648 | 4/2009 |
| KR | 10-2009-0042073 | 4/2009 |

OTHER PUBLICATIONS

Glossary of medical education terms, Institute of International Medical Education. http://www.iime.org/glossary.htm Accessed on Jan. 2013.*
Proksch E. The role of emollients in the management of diseases with chronic dry skin. Skin Pharmacol Physiol 21:75-80, 2088.*
Qiu et al. Structure elucidation and sulfated derivatives preparation of two alpha-D-glucans from Gastrodia elata B1 and their anti-dengue virus bioactivities. Carbohydrate Res 342:2230-2236, 2007.*
International Search Report for PCT/KR2010/003348, mailed Feb. 22, 2011.
Derwent Data Base; Abstract of Cosmetic Composition for Improving Skin Troubles Caused by Stresses and Enlarging the Sleeping Time Containing the Extract of *Chamaecyparis Obtusa*, Apr. 21, 2008.
Chinese Office Action and English translation in CN 201080020473.8 dated Oct. 29, 2012.

\* cited by examiner

*Primary Examiner* — Wu-Cheng Winston Shen
*Assistant Examiner* — Yih-Horng Shiao
(74) *Attorney, Agent, or Firm* — Nixon & Vanderhye P.C.

(57) ABSTRACT

The present invention relates to a composition for skin external application containing a *Chamaecyparis obtusa* polysaccharide as an active ingredient, and more particularly to a composition for skin external application containing a *Chamaecyparis obtusa* polysaccharide, which improves skin elasticity and reduces wrinkles by promoting collagen production, shows an excellent skin-whitening effect by inhibiting melanogenesis, improves skin moisturization by promoting keratinocyte differentiation, and has excellent anti-inflammatory and skin regeneration effects.

12 Claims, 1 Drawing Sheet

COMPOSITION CONTAINING *CHAMAECYPARIS OBTUSA* POLYSACCHARIDES TO BE EXTERNALLY APPLIED TO THE SKIN

This application is the U.S. national phase of International Application No. PCT/KR2010/003348, filed 27 May 2010, which designated the U.S. and claims priority to KR Application No. 10-2009-0047317, filed 29 May 2009, the entire contents of each of which are hereby incorporated by reference.

TECHNICAL FIELD

The present invention relates to a composition for skin external application containing a *Chamaecyparis obtusa* polysaccharide as an active ingredient, and more particularly to a composition for skin external application containing a *Chamaecyparis obtusa* polysaccharide, which improves skin elasticity and reduces wrinkles by promoting collagen production, shows an excellent skin-whitening effect by inhibiting melanogenesis, improves skin moisturization by promoting keratinocyte differentiation, and has excellent anti-inflammatory and skin regeneration effects.

BACKGROUND ART

Human skin undergoes changes with age due to a variety of internal and external factors. Specifically, with respect to the internal factors, the secretion of various hormones that regulate metabolism is reduced, the function of immunocytes and the activity of cells decline, and thus the biosynthesis of immune proteins and structural proteins that constitute a living body is reduced. With respect to the external factors, as the amount of ultraviolet rays reaching the earth's surface is increasing due to destruction of the ozone layer, and as environmental pollution becomes ever more serious, free radicals and reactive oxygen species increase. As a result, skin thickness decreases, wrinkles increase, skin elasticity decreases, the skin color becomes darker, skin troubles frequently arise, and age spots, freckles and dark spots also increase.

As aging progresses, the content and arrangement of collagen, elastin, hyaluronic acid and glycoprotein that constitute the skin are changed or decrease, and oxidative stress occurs due to free radicals and reactive oxygen species. Also, it is known that, as aging progresses or by the action of UV rays, in most cells of the skin, the biosynthesis of cyclooxygenase-2 (Cox-2) producing proinflammatory cytokines known to cause inflammation increases, the biosynthesis of matrix metalloproteinase (MMP) which degrades skin tissue increases due to these inflammatory factors, and the production of nitric oxide (NO) by inducible nitric oxide synthase (iNOS) increases. In other words, due to intrinsic aging that naturally progresses, the activity of cells is reduced, and the biosynthesis of substrates is reduced due to minute inflammation. In addition, due to external factors such as an increase in stress caused by various harmful pollutants and an increase in reactive oxygen species caused by the sunlight, degradation and denaturation are accelerated, and thus the skin matrix is broken and becomes thinner, while various symptoms of skin aging appear. For this reason, many studies on active ingredients that can prevent and ameliorate such aging phenomena are being conducted.

Various factors are involved in determining the human skin color. Among them, the activity of melanocytes producing melanin pigments, the distribution of blood vessels, the thickness of the skin, and the presence or absence of pigments such as carotenoids and bilirubin in the human body, are important.

The most important factor among them is the black pigment melanin which is produced by the action of various enzymes such as tyrosinase in melanocytes. The production of the melanin pigment is influenced by genetic factors, physiological factors associated with hormone secretion and stress, and environmental factors such as UV radiation.

The melanin pigment, which is produced by melanocytes, is a phenolic polymer in the form of a black pigment/protein composite and has useful functions to protect skin organs under the dermis by blocking UV light radiation from the sun and simultaneously to capture free radicals from the skin, thus protecting proteins and genes in the skin.

Melanin produced in the skin due to intrinsic and extrinsic stresses as described above is a stable material and does not disappear until it is discharged to the outside through skin keratinization, even when the stresses disappear. However, if melanin is produced larger than required, hyperpigmentation such as freckles and spots is induced, leading to unfavorable results in the sense of beauty.

These days, women in oriental countries prefer a white and clean skin like white gem and consider this skin as an important beauty standard. For this reason, the demand to solve therapeutic and cosmetic problems for hyperpigmentations has increased.

To satisfy this demand, ascorbic acid, kojic acid, arbutin, hydroquinone, glutathione, or derivatives thereof, or substances having tyrosinase inhibitory activity, have been used in cosmetics or medical drugs. However, the use thereof has been limited due to insufficient whitening effects and various problems, such as skin safety, and formulation and stability, which occur when they are added to cosmetics.

The most important function of the epidermis which is the outermost layer of the skin is to protect the skin from various external stimuli (physical and chemical stimuli such as chemicals, pollutants, dry environment and UV radiation) and to prevent excessive loss of water through the skin. This protective function can be maintained only when the horny layer consisting of keratinocytes are formed normally. The horny layer (stratum corneum), the outermost layer of the epidermis, is formed from keratinocytes and consists of terminally differentiated keratinocytes surrounded by lipid layers. Keratinocytes are the cells generated as a result of the process in which basal cells that continuously proliferate in the lowest layer of the epidermis move up toward the skin's surface while they undergo a series of structural and functional changes. After a given period, old keratinocytes are shed from the skin and replaced by new keratinocytes. This repeated process is called "differentiation of epidermal cells" or "keratinization". During the keratinization process, keratinocytes form the horny layer, while they produce natural moisturizing factors (NMFs) and intercellular lipids (ceramides, cholesterols and fatty acids), such that the horny layer has firmness and softness to function as a skin barrier.

However, this horny layer can easily lose its functions due to lifestyle factors such as excessive face washing or bathing, environmental factors such as dry atmosphere or pollutants, and intrinsic diseases such as atopy or geriatric skin disease. In fact, due to various factors which have increased recently, more and more people are suffering from dry skin symptoms and various disorders. Thus, in order to keep the skin moisturized at a suitable level, many studies focused on supplying water from outside or preventing loss of water from the body have been conducted. In fact, various kinds of moisturizers having water retention capability have been developed and used mainly in the cosmetic field.

However, as harmful factors to the human body gradually increase in the living environment and an aged population increases rapidly, the turnover rate of the horny layer becomes slower, and the lipid synthesis capability of keratinocytes is reduced, or the division, growth and differentiation of cells in the epidermis become inefficient. As a result, more people have such skin conditions that the quantity of moisturizing factors and lipids is insufficient and the function of the horny layer is not maintained (i.e., the skin barrier function is not maintained).

The abnormality in the division and differentiation of epidermal cells causes various skin diseases, including xeroderma, atopy and psoriasis. Such diseases can be slightly relieved with existing moisturizers having water retention capability only, but it is difficult to expect fundamental cure of the diseases.

Skin disease refers to all disorders occurring on the skin of animals including humans. Inflammatory skin disease refers to a disease that involves a series of clinical signs and symptoms, such as itching, edema, erythema and stripping, due to various stimulating factors which cause a series of inflammatory reactions in the skin epidermis. Known inflammatory skin diseases include atopic dermatitis, contact dermatitis, seborrhoic dermatitis, acne, etc.

For the treatment of the inflammatory skin diseases, antihistamine agents, vitamin ointments and adrenal cortical hormones have been used to date. However, such drugs mostly have temporary effects and show severe side effects in some cases.

Meanwhile, the skin functions as a barrier that protects the body from the external environment. When the skin is wounded, the site of the wound site is filled with blood by natural healing action, and a decrease in platelet granules and the activation of hageman factor is initiated so that a wound healing process takes place. The coagulation of blood is a temporary defensive action that protects exposed wound tissues and provides a basis on which cells can migrate during a healing process (Lee S H A S, Jung S G. Skin Barrier. Seoul: Ryo Moon Gak, 2004).

A wound healing process is generally divided into four phases: inflammatory phase, re-epithelization phase, proliferative phase, and maturation phase. During the inflammatory phase, immune cells appear at the wound site, in which the cells migrated from to the wound site. Then, growth factors, which induce the formation of granular tissue, and signaling substances, are secreted. In a state in which there is no serious infection, the inflammatory phase is generally short (Care KRGf. Advances in wound Care. Seoul: Korea Medical Book Publisher, 2002). The inflammatory phase is essential for the wound healing process.

The proliferative phase occurs similarly to the re-epithelization phase and is characterized in that granular tissues are formed at the wound site (Kubo K K Y. Spongy matrix of hyaluronic acid and collagen as a cultured dermal substitute: evaluation in an animal test. J Artif Organs 2003; 6(1):64-70). Granular tissues are composed of a composition of extracellular matrix elements such as immaturity collagen, fibronectin and hyaluronic acid, as well as fibroblasts and inflammatory cells, and it is important in wound healing that these granular tissues rapidly fill the wound site and have a textured structure. While the exfoliated wound surface is covered by a layer of keratinocytes, a new epidermis is produced and the epithelial layer is reformed. The cells move upward through the wound from the wound edge or the dermal debris of the skin and start to migrate through the scab and living connective tissue.

When re-epithelization of the wound is completed, a series of processes in which the wound area is reduced by an increase in connective tissue and remodeling occur.

Then, during the maturation phase, the coagulated cells and capillary vessels of the tissues in the repair phase gradually disappear, and if such tissues are excessively formed or are not normally degraded, scars will be formed. This is a general wound healing process. Not only rapidly healing a wound, but also healing the wound without side effects or scar, is important in the wound healing process. For this reason, it is more important that tissue cells are filled in a balanced manner while inhibiting inflammation and regulating the expression of growth factors, and efforts to find substances having such effects have been continuously made.

Studies on *Chamaecyparis obtusa* have been focused on the effects of phytoncide contained in *Chamaecyparis obtusa* essential oil. Phytoncide is a compound word of "phyton" which means a plant and "cide" which means "exterminate". It is also called "exterminated by plant" and can be said to be a "woody scent". It is a substance which is released or secreted by plants to resist pathogens, harmful insects, and molds. If a person takes phytoncide, stress will be reduced, the intestinal and cardiopulmonary functions will be enhanced and the bacteria killing action will also take place. Such phytoncide is composed of phenolic compounds such as terpenes, alkaloids, glycosides, etc., and thus can be extracted using organic solvents. Therefore, the phytoncide of *Chamaecyparis obtusa* trees is contained in a *Chamaecyparis obtusa* essential oil extracted from *Chamaecyparis obtusa* trees.

Although cosmetic compositions for improving skin conditions containing general *Chamaecyparis obtusa* extracts are known, a *Chamaecyparis obtusa* polysaccharide and its effects on anti-aging, a reduction in skin wrinkles, an improvement in skin elasticity, skin whitening, skin moisturization, prevention and amelioration of dry skin diseases, anti-inflammation, skin regeneration, and the like are not known.

DISCLOSURE

Technical Problem

Accordingly, the present inventors have made efforts to find components which can protect the skin from an external harmful environment or UV rays to prevent skin aging and improve skin conditions, and as a result, have found that a composition for skin external application containing a *Chamaecyparis obtusa* polysaccharide as an active ingredient have excellent effects on improvement of skin elasticity, reduction of skin wrinkles, skin whitening, skin moisturization, inflammatory inhibition and skin regeneration, thereby completing the present invention.

Therefore, it is an object of the present invention to provide a composition for skin external application containing a *Chamaecyparis obtusa* polysaccharide as an active ingredient.

Technical Solution

To achieve the above object, the present invention provides a composition for skin external application containing a *Chamaecyparis obtusa* polysaccharide as an active ingredient.

Advantageous Effects

The inventive composition for skin external application containing a *Chamaecyparis obtusa* polysaccharide as an active ingredient promotes collagen production, inhibits melanogenesis, promotes keratinocyte differentiation, reduce skin inflammatory responses and skin irritation to provide anti-aging effect, and has very excellent effects on reduction of skin wrinkles, improvement of skin elasticity, skin whitening, skin moisturization, prevention and amelioration of dry skin diseases, anti-inflammation, skin regeneration, etc.

BEST MODE

The present invention provides a composition for skin external application containing a *Chamaecyparis obtusa* polysaccharide as an active ingredient.

*Chamaecyparis obtusa* that is used in the present invention is an evergreen tall tree belonging to the family Cupressaceae and grows to a height of 50 m and a diameter of 2 m. Its branches spread horizontally to form a conical crown, and its bark is red brown in color and splits vertically and exfoliates. It grows straight so that it has a very wide range of applications. It is mainly used in construction materials, civil engineering materials, ships, or chip materials.

The *Chamaecyparis obtusa* polysaccharide that is used as the active ingredient in the composition of the present invention promotes collagen production, inhibits the expression of MMP-1 to prevent skin aging, reduces skin wrinkles and improves skin elasticity. Also, it inhibits melanogenesis to provide excellent skin whitening effects, induces keratinocyte differentiation to increase skin moisturization, thereby preventing and ameliorating dry skin diseases, and inhibits the biosynthesis of cyclooxygenase-2 induced by inflammatory response inducers to exhibit excellent effects on reductions in skin inflammation, skin irritation and skin troubles.

Thus, the inventive composition for skin external application containing a *Chamaecyparis obtusa* polysaccharide as an active ingredient is very useful for anti-aging, reduction of skin wrinkles, improvement of skin elasticity, skin whitening, skin moisturization, prevention and amelioration of dry skin diseases such as atopy, anti-inflammation, skin regeneration, prevention and amelioration of skin troubles, and the like.

A general *Chamaecyparis obtusa* extract is a mixture of extracts obtained by extracting various components from *Chamaecyparis obtusa* using, for example, water or an aqueous ethanol solution, and when it is used in a composition for skin external application, it causes problems such as discoloration or pigmentation due to the chlorophyll, etc. contained therein. However, the *Chamaecyparis obtusa* polysaccharide that is used in the present invention can solve the problems of the *Chamaecyparis obtusa* extract, because it consists mainly of polysaccharides obtained by applying a special separation process to the *Chamaecyparis obtusa* extract.

The *Chamaecyparis obtusa* polysaccharide of the present invention can be prepared by a method known in the art, and a method for preparing the same is not specifically limited. As a specific example, a solvent extraction method is used to remove chlorophyll from dried *Chamaecyparis obtusa* leaves. As the extraction solvent, one or more selected from the group consisting of hexane, ethanol and methanol are preferably used. More preferably, ethanol is used in order to remove a problem of toxicity which can occur due to the remaining chlorophyll when the *Chamaecyparis obtusa* polysaccharide is used in the cosmetic composition.

Dried *Chamaecyparis obtusa* leaves are added to the solvent and sufficiently stirred at room temperature, after which the solvent containing chlorophyll dissolved therein is removed by centrifugation. The resulting *Chamaecyparis obtusa* leaf residue is dried, whereby a *Chamaecyparis obtusa* leaf containing no chlorophyll can be obtained.

In order to extract an aqueous soluble active ingredient from the prepared *Chamaecyparis obtusa* leaf residue, a hot-water extraction process is carried out. The hot-water extraction process is preferably carried out at a temperature of 30~40° C. If the hot-water extraction process is carried out at a temperature higher than 40° C., thermal denaturation can occur due to the high temperature, and if it is carried out at a temperature lower than 30° C., the polysaccharide will not be sufficiently extracted. The hot-water extraction time is preferably 6-8 hours. If the extraction time is longer than 8 hours, contamination by microorganisms can occur, and if it is shorter than 6 hours, the polysaccharide will not be sufficiently extracted. The extract resulting from the hot-water extraction is filtered using a filtration device, and then concentrated under reduced pressure.

In order to separate only the polysaccharide from the hot-water extract, ultra-filtration and an ethanol precipitation reaction are carried out. The polysaccharide has a molecular weight of 100,000 dalton or more which is much higher than the molecular weight of free proteins. The ultra-filtration process is carried out using this difference in molecular weight, whereby the content of the *Chamaecyparis obtusa* polysaccharide can be increased. Also, the ultra-filtration process is a continuous process and has advantages in that the separation of low-molecular-weight substances and the concentration of the filtrate can be carried at the same time and in that a problem of thermal denaturation does not occur because the process is carried out at room temperature.

Then, ethanol is added slowly to the ultra-filtration concentrate, thereby carrying out the ethanol precipitation reaction. Herein, the rate of ethanol added is preferably 100-200 Ml/min. If the rate of ethanol added is higher than 200 Ml/min, the resulting particles can become excessively large or can be agglomerated. After completion of the ethanol precipitation reaction, the ethanol is removed, and the remaining *Chamaecyparis obtusa* polysaccharide is vacuum-dried at a temperature of 40-50° C., whereby a *Chamaecyparis obtusa* polysaccharide can be obtained as powder.

The *Chamaecyparis obtusa* polysaccharide of the present invention is preferably contained in an amount of 0.001-10 wt % based on the total weight of the composition for skin external application. If the content of the *Chamaecyparis obtusa* polysaccharide is less than 0.001 wt %, it will have an insignificant effect so that it cannot act as the active ingredient, and if the content is more than 10 wt %, it can cause a problem in terms of formulation stability.

The composition for skin external application according to the present invention contains a cosmetically and skin-scientifically acceptable medium or base. The composition may be formulated as a preparation for local application. Examples of formulations for local application include a solution, a gel, a solid, a dough anhydride, an emulsion prepared by dispersing an oil phase in a water phase, a suspension, a microemulsion, microcapsules, microgranules, ionic (liposome) and non-ionic vesicles, cream, skin lotion, an ointment, powder, a spray, and a conceal stick. In addition, the composition of the present invention can be formulated according to a conventional method known in the art. Also, the composition for skin external application according to the present invention can be formulated as a foam composition or an aerosol composition further containing a compressed propellant.

The composition for skin external application according to the present invention may contain additives which are conventionally field in the cosmetic field or the skin science field, for example, a fatty substance, an organic solvent, a solubilizing agent, a thickener, a gelling agent, a softener, an antioxidant, a suspending agent, a stabilizer, a foaming agent, an aromatic, a surfactant, water, an ionic or non-ionic emulsifying agent, a filler, a sequestering agent, a chelating agent, a preservative, vitamins, a blocker, a moisturizing agent, essential oil, a dye, a pigment, a hydrophilic or hydrophobic activator, a lipid vesicle, or other components which are generally used in cosmetics. These additives are contained in amounts which are generally used in the cosmetic field or the skin science field.

There is no particular limitation on the formulation of the inventive composition for skin external application containing the *Chamaecyparis obtusa* polysaccharide. It may be formulated into cosmetic products, for example, skin lotion, astringent lotion, milk lotion, nourishing cream, massage cream, essence, eye cream, eye essence, cleansing cream, cleansing foam, cleansing water, pack, powder, body lotion, body cream, body oil and body essence.

The composition for skin external application according to the present disclosure may be a pharmaceutical composition. The pharmaceutical composition may contain pharmaceutical additives such as antiseptics, stabilizing agents, hydrating agents, emulsification promoters or salts and/or buffers for osmotic control and may further contain other therapeutically useful substances. The pharmaceutical composition may be formulated into lotion, cream, ointment, gel, or the like.

The pharmaceutical composition is preferably administered transdermally. The administration dose of the *Chamaecyparis obtusa* polysaccharide which is the active ingredient of the pharmaceutical composition may vary depending on the age, sex and bodyweight of the subject in need of treatment, the particular disease to be treated or pathological conditions thereof, severity of the disease or pathological conditions, administration route, and discretion of a physician or pharmacist. The administration dose may be determined by those skilled in the art in consideration of those factors. A general administration dose is in the range from about 0.0001 mg/kg/day to about 2000 g/kg/day.

MODE FOR INVENTION

Hereinafter, the construction and effect of the present invention will be described in further detail with reference to examples and experimental examples. It is to be understood, however, that these examples and test examples are for illustrative purposes and are not to be construed to limit the scope of the present invention.

Preparation Example 1

Preparation of *Chamaecyparis obtusa* Polysaccharide 10 l of ethanol was added to 1 kg of dried *Chamaecyparis obtusa* leaves which were then stirred at room temperature for 24 hours, after which the solvent was removed by centrifugation. The resulting *Chamaecyparis obtusa* leaf residue was extracted in hot water at 30° C. for 7 hours, and the resulting hot-water extract was extracted using a filter press device (diatomaceous earth filtration) and collected, after which it was concentrated under reduced pressure at 50° C. to reach 1/10 of the initial volume. Then, the concentrate was ultra-filtered (molecular weight cut off: 1,000 Da) to remove low-molecular-weight free proteins, and ethanol having a volume 5 times that of the resulting ultra-filtration concentrate was added slowly to the concentrate at a rate of 100 Ml/min, thereby carrying out an ethanol precipitation reaction. The precipitated *Chamaecyparis obtusa* polysaccharide was vacuum-dried at 45° C., thereby obtaining 53 g of a *Chamaecyparis obtusa* polysaccharide as powder.

Experimental Example 1

Type I Procollagen Assay

Human normal fibroblasts were cultured in a 12-well culture plate at a concentration of $10^5$ cells/well, and then the medium was replaced with each of media containing 1 ppm, 10 ppm and 50 ppm of the *Chamaecyparis obtusa* polysaccharide obtained in Preparation Example 1. As a positive control, TGF-β (Human Transforming Growth Factor-β1, Roche Co.) was used. At 3 days of culture, the cells were harvested, and the amount of type I procollagen produced in the cells was measured by an ELISA assay. Each of the measurement values was calculated relative to 0 for a control containing no *Chamaecyparis obtusa* polysaccharide and 100 for the positive control, and the results of the calculation are shown in Table 1 below.

TABLE 1

| | Type I procollagen biosynthesis (%) |
|---|---|
| Negative control | 0 |
| *Chamaecyparis obtusa* polysaccharide (1 ppm) | 2 |
| *Chamaecyparis obtusa* polysaccharide (10 ppm) | 12 |
| *Chamaecyparis obtusa* polysaccharide (50 ppm) | 21 |
| TGF-β (10 ng/Ml) | 100 |

As can be seen in Table 1 above, in the normal human fibroblast monolayer culture system, the *Chamaecyparis obtusa* polysaccharide promoted the production of type I procollagen in a concentration-dependent manner compared to the negative control. This suggests that the Normal human fibroblast monolayer culture system of the present invention promotes collagen production to inhibit the decrease in collagen caused by skin aging, indicating that it has an excellent anti-aging effect.

Experimental Example 2

Analysis of Inhibition of MMP-1 Biosynthesis

Human normal fibroblasts were cultured in a 12-well culture plate at a concentration of $10^5$ cells/well, and then irradiated with 40 mJ/cm² of UV-B, after which the medium was replaced with a medium containing each of 1 ppm, 10 ppm and 50 ppm of the *Chamaecyparis obtusa* polysaccharide obtained in Preparation Example 1. At 2 days of culture, the cells were harvested, and the amount of MMP-1 (matrix metalloproteinase I) produced in the cells was measured by an ELISA assay. As a positive control, retinoic acid (RA, Sigma, USA) was used. Each of the measurement values was calculated relative to 0 for a control containing no *Chamaecyparis obtusa* polysaccharide and which was not irradiated with UV-B. The results of the calculation are shown in Table 2 below.

TABLE 2

| | MMP-1 biosynthesis (%) |
|---|---|
| Not irradiated with UV (control) | 100 |
| Irradiated with UV | 152 |
| Irradiated with UV + *Chamaecyparis obtusa* polysaccharide (1 ppm) | 145 |
| Irradiated with UV + *Chamaecyparis obtusa* polysaccharide (10 ppm) | 134 |
| Irradiated with UV + *Chamaecyparis obtusa* polysaccharide (50 ppm) | 105 |
| Irradiated with UV + RA (10 μM) | 45 |

As can be seen in Table 2 above, in the normal human fibroblast monolayer culture system, the *Chamaecyparis obtusa* polysaccharide significantly inhibited MMP-1 biosynthesis induced by UV-B. Also, when the *Chamaecyparis obtusa* polysaccharide was used at a concentration of 50 ppm to treat the cells, it inhibited MMP-1 biosynthesis to a level similar to that of the control which was not irradiated with UV.

Thus, it can be seen that the *Chamaecyparis obtusa* polysaccharide according to the present invention inhibits the biosynthesis inhibits the biosynthesis of the skin tissue degradation enzyme MMP-1 resulting from intrinsic aging or external environmental factors, thereby preventing various symptoms associated with skin aging in which the skin matrix is broken and becomes thinner, and inhibiting a decrease in skin collagen to reduce skin wrinkles.

Experimental Example 3

Effect on Reduction of Human Skin Wrinkles

Each of nourishing cream (Example 2 in Table 3) containing the *Chamaecyparis obtusa* polysaccharide and nourishing cream (Comparative Example 1 in Table 3) containing no *Chamaecyparis obtusa* polysaccharide was applied to forty 30-50-year-old test subjects having facial wrinkles, and the effects of the creams on the reduction of skin wrinkles were comparatively evaluated.

| Components | Example 1 (wt %) | Comparative Example 1 (wt %) |
|---|---|---|
| *Chamaecyparis obtusa* polysaccharide (Preparation Example 1) | 0.1 | — |
| Beeswax | 10 | 10 |
| Polysorbate 60 | 1.5 | 1.5 |
| PEG 60 hydrogenated castor oil | 2 | 2 |
| Sorbitan sesquioleate | 0.5 | 0.5 |
| Liquid paraffin | 10 | 10 |
| Squalane | 5 | 5 |
| Capylic/capric triglyceride (Estasan: Uniqema) | 5 | 5 |
| Glycerin | 5 | 5 |
| Butylene glycol | 3 | 3 |
| Propylene glycol | 3 | 3 |
| Triethanolamine | 0.2 | 0.2 |
| Preservative, pigment and fragrance | q.s. | q.s. |
| Purified water | Balance | Balance |

In this Experimental Example, Example 1 was applied on the left side of the face of the subjects for 3 months, and Comparative Example 1 was applied on the right side for 3 months. The skin conditions of both sides of the face were measured before application of the creams, and after 3-month application of the creams, the conditions of the same portions were measured again, thus measuring changes in skin wrinkles. More specifically, in a constant-temperature and constant-humidity chamber at a temperature of 24° C. and a relative humidity of 40%, wrinkles at the outer corner of the eyes were reproduced with a replica, and the facial wrinkles were measured with a Visiometer system (C+K Inc.). The change in skin wrinkles was calculated according to the following equation 1.

$$\text{Change } (\Delta \%) \text{ in skin wrinkles} = (Tdi - Tdo)/Tdo \times 100 \quad \text{[Equation 1]}$$

wherein "Tdi" is a value measured after 90 days of allocation, and "Tdo" is a value measured before application.

In the results of calculating the change in skin wrinkles according to the equation 1, the skin wrinkles at the portion applied with Comparative Example 1 containing no *Chamaecyparis obtusa* polysaccharide showed a decrease of 5.3±4% (mean±standard deviation), whereas the skin wrinkles at the portion applied with Example 1 containing the *Chamaecyparis obtusa* polysaccharide showed a decrease of 30±8%.

As can be seen from the above results, Example 1 containing the *Chamaecyparis obtusa* polysaccharide of the present invention reduced skin wrinkles about 6 times more than Comparative Example 1 containing no *Chamaecyparis obtusa* polysaccharide. This suggests that Example 1 containing the *Chamaecyparis obtusa* polysaccharide according to the present invention had excellent effects on the reduction of skin wrinkles.

Experimental Example 4

Effect of Improving Skin Elasticity in Human Body

The effects of Example 1 and Comparative Example 1 on the improvement of skin elasticity were measured. 40 women, 30-50 years old, were divided into 2 groups. The faces of the subjects in each of the groups were applied with the nourishing creams of Example 1 and Comparative Example 1 two times every day for 12 weeks, and then the skin elasticity of the faces was measured using Cutometer SEM 575 (C+K Electronic Co., Germany).

The skin elasticity value of the portion applied with Comparative Example 1 was 0.21±0.14 (mean±standard deviation), whereas the skin elasticity value of the portion applied with Example 1 was 0.30±0.10.

As can be seen from the above results, Example 1 containing the *Chamaecyparis obtusa* polysaccharide of the present invention showed a skin elasticity improvement effect which was about 30% higher than that of Comparative Example 1 containing no *Chamaecyparis obtusa* polysaccharide.

Experimental Example 5

Analysis of Melanin Production Inhibitory Effect Using Mouse Melanocytes

Mouse melanocytes were used to examine the melanin production inhibitory effect of the *Chamaecyparis obtusa* polysaccharide of the present invention. First, C57BL/6 mouse melanocytes (Mel-Ab cells) (Dooley, T. P. et al, Skin pharmacol, 7, pp 188-200) were cultured in DMEM (Dulbeccos modified Eagles media), containing 10% fetal bovine serum, 100 nM 2-O-tetradecanoyphorbol-13-acetate and 1 nM cholera toxin, in conditions of 37° C. and 5% $CO_2$. The cultured Mel-Ab cells were detached with 0.25% trypsin- EDTA and cultured in a 24-well culture plate at a concentration of $10^5$ cells/well. Then, from 2 days of culture, each of 10 ppm, 50 ppm and 100 ppm of the *Chamaecyparis obtusa* polysaccharide was continuously added thereto and cultured for 3 days. Herein, arbutin was used as a positive control. Then, the media were removed, and the cells were washed with PBS and lysed with 1N sodium hydroxide. The lysed cells were measured for absorbance at 400 nm, and based on the measured absorbance, the inhibition (%) of melanin production was calculated according to the following equation 2. The results of the calculation are shown in Table 4 (Dooley's method).

Inhibition (%) of melanin production=100−(absorbance of each test material/absorbance of control×100)     [Equation 2]

TABLE 4

|  | Inhibition (%) of melanin production |
|---|---|
| Untreated (control) | 0 |
| *Chamaecyparis obtusa* polysaccharide (10 ppm) | 5 |
| *Chamaecyparis obtusa* polysaccharide (50 ppm) | 20 |
| *Chamaecyparis obtusa* polysaccharide (100 ppm) | 53 |
| Arbutin (100 ppm) | 52 |

As can be seen in Table 4 above, the *Chamaecyparis obtusa* polysaccharide according to the present invention inhibited melanin production in a concentration-dependent manner. Also, 100 ppm of the *Chamaecyparis obtusa* polysaccharide showed a melanin production inhibition rate similar to that of the same concentration of arbutin. This suggests that the *Chamaecyparis obtusa* polysaccharide of the present invention showed an excellent skin whitening effect by effectively inhibiting melanin production.

Experimental Example 6

Whitening Effect on Human Skin

In order to examine the whitening effect of the *Chamaecyparis obtusa* polysaccharide of the present invention on the human skin, the following test was carried out. First, on 12 healthy men as subjects, a 1.5-cm perforated opaque tape was attached to the upper arm portion of the subjects, and then the attached portion was radiated with UVB at a dose about 1.5-2 times the minimal erythema dose of each subject to induce skin darkening.

After the UV radiation, each of the *Chamaecyparis obtusa* polysaccharide (test material) and hydroquinone was applied to the UV-radiated portion, and a change in the state of the applied portion was observed for 10 weeks in comparison with a control portion applied with a solvent alone. The color of the skin was measured with a colorimeter CR2002 (Japan, Minolta). Then, the difference ($\Delta L^*$) in skin color between the time point of initiation of application and the time point of completion of application (after 10 weeks) of each test material was calculated according to the following equation 3, and the results of the calculation are shown in Table 5 below.

Meanwhile, the skin whitening effect is evaluated by measuring the $\Delta L^*$ value between the sample-applied portion and the control portion. A $\Delta L^*$ value of about 2 indicates that pigmentation is clearly relieved, and if it is more than about 1.5, it can be judged to have a whitening effect.

Difference ($\Delta L^*$) skin color=$L^*$value at the time of completion of application−$L^*$value at the time of initiation of application     [Formula 3]

TABLE 5

| Test material | Difference ($\Delta L^*$) in skin color |
|---|---|
| *Chamaecyparis obtusa* polysaccharide | 1.75 ± 0.17 |
| Hydroquinone (positive control) | 1.89 ± 0.15 |
| Solvent (negative control) | 0.51 ± 0.13 |

As shown in Table 5 above, the *Chamaecyparis obtusa* polysaccharide of the present invention showed skin-color brightness similar to that of hydroquinone. This suggests that the *Chamaecyparis obtusa* polysaccharide of the present invention reduces pigmentation caused by UV rays and has an excellent skin whitening effect.

Experimental Example 7

Induction of Differentiation of Human Keratinocytes

The effect of the *Chamaecyparis obtusa* polysaccharide of the present invention on the promotion of cell differentiation was examined by measuring the amount of CE (cornified envelop) produced during differentiation of keratinocytes and a human keratinocyte cell line (HaCaT).

Primarily cultured human keratinocytes were placed in a culture flask and allowed to adhere to the bottom of the flask, and then calcium and the *Chamaecyparis obtusa* polysaccharide were added to the culture media at varying concentrations. The cells were cultured for 5 days to a confluency of about 70-80%. The cultured cells were harvested and washed with PBS (phosphate buffered saline), and then 1 ml of 10 mM Tris-HCl buffer (pH 7.4), containing 2% SDS (sodium dodecyl sulfate) and 20 mM DTT (dithiothreitol), was added to the cells. The cell solution was sonicated, boiled and centrifuged, and the resulting precipitate was suspended in 1 ml of PBS and measured for absorbance at 340 nm. Meanwhile, a portion of the solution after the sonication was taken and measured for its protein content, and the measured value was used as a standard for evaluating the degree of cell differentiation. A low calcium (0.03 mM)-treated group and a high calcium (1.2 mM)-treated group were used as a negative control groups and a positive control group, respectively. Each of the measurement values was calculated relative to 100 for the negative control (low calcium concentration), and the results of the calculation are shown in Table 6 below.

TABLE 6

| Test material |  | Differentiation (%) of keratinocytes |
|---|---|---|
| Control | Low calcium-treated group ($Ca^{2+}$ 0.03 mM) | 100 |
|  | High calcium-treated group ($Ca^{2+}$ 1.2 mM) | 215 |
| *Chamaecyparis obtusa* polysaccharide | 1 ppm | 122 |
|  | 10 ppm | 125 |
|  | 100 ppm | 135 |

As can be seen from the results in Table 6 above, the *Chamaecyparis obtusa* polysaccharide of the present invention promoted keratinocyte differentiation in a concentration-dependent manner. Thus, it can be seen that the *Chamaecyparis obtusa* polysaccharide of the present invention promotes keratinocyte differentiation and normalizes the turnover cycle of the epidermis to enhance skin moisturization.

Experimental Example 8

Effect on Expression of Transglutaminase in Human Keratinocytes

Human skin cells were placed in a 96-well plate at a concentration of $5\times10^4$ cells/well and attached to the plate for 24 hours. The attached skin cells were treated with the test material, and after 2 days, the medium was removed, and the cells were stored in a refrigerator at 20° C. The cells were frozen and thawed twice, disrupted and treated with acetone:ethanol (1:1, v/v), stored at −20° C. The treated cells were left to stand at 4° C. for 30 minutes to immobilize the cells. Then, the cells were left to stand at room temperature to evaporate the organic solvent and were blocked with 1% bovine serum albumin. The blocked cells were treated with transglutaminase antibody (primary antibody) and HRP anti-mouse antibody (secondary antibody), and the color development of the cells was carried out by the addition of OPD (o-phenyldiamine). The expression level of transglutaminase in the cells was measured by measuring the absorbance at 490 nm, and the correction was carried out by measuring the background at 630 nm. A low calcium (0.03 mM)-treated group and a high calcium (1.2 mM)-treated group were used as a negative control group and a positive control group, respectively. Each of the measurement values was calculated relative to 100 for the negative control (low calcium concentration), and the results of the calculation are shown in Table 7 below.

TABLE 7

| | Test material | Expression (%) of transglutaminase |
|---|---|---|
| Control | Low calcium-treated group ($Ca^{2+}$ 0.03 mM) | 100 |
| | High calcium-treated goup ($Ca^{2+}$ 1.2 mM) | 138 |
| | 1 ppm | 105 |
| | 10 ppm | 123 |
| | 100 ppm | 145 |

As can be seen from the results in Table 7 above, the *Chamaecyparis obtusa* polysaccharide of the present invention increased the expression of transglutaminase in a concentration-dependent manner compared to the negative control, and the group treated with 100 ppm of the *Chamaecyparis obtusa* polysaccharide showed a higher expression of transglutaminase than the positive control (high calcium-treated group). Thus, it can be seen that the *Chamaecyparis obtusa* polysaccharide of the present invention shows an excellent skin moisturization effect by promoting the expression of transglutaminase in keratinocytes.

Experimental Example 9

Increase in Skin Moisturizing Ability in Human Body

Fifty 50-60-years old men and women having xerosis cutis were divided into two groups, and the faces of the subjects in each of the groups were applied with Example 1 and Comparative Example 1 twice every day for 4 weeks. Before the initiation of application, at 1 week, 2 weeks and 4 weeks after the initiation of application and at 2 weeks after the end of application (a total of 6 weeks), the moisture content of the skin of the subjects was measured with a koniometer in constant temperature and constant humidity conditions (24° C. and 40% relative humidity). The test results were expressed as the percentages of increases in values, measured after application, relative to koniometer values, measured immediately before the initiation of application. The test results are shown in Table 8 above.

TABLE 8

| | Increase (%) in moisture content | | | |
|---|---|---|---|---|
| Test material | After 1 week | After 2 weeks | After 4 weeks | After 6 weeks |
| Example 1 | 35 | 45 | 49 | 35 |
| Comparative Example 1 | 31 | 34 | 34 | 15 |

As can be seen in Table 8 above, the group applied with Example 1 containing the *Chamaecyparis obtusa* polysaccharide showed an increase in skin moisture content at all the time points of measurement compared to the group applied with Comparative Example 1. The value obtained by measuring the skin moisture content at 2 weeks after stopping the application of the nourishing cream of Example 1 (after a total of 6 weeks) was similar to the value measured at 1 week after application, whereas the group applied with Comparative Example 1 showed a rapid decrease in skin moisture content when the application of Comparative Example 1 was stopped. Thus, it can be seen that the composition containing the *Chamaecyparis obtusa* polysaccharide according to the present invention increases the skin moisture content and maintains the skin moisture content for a given period of time, even when the application thereof is stopped.

Experimental Example 10

Effect of Inhibiting Cyclooxygenase-2 (Cox-2) Biosynthesis Induced by LPS (Lipopolysaccharide)

Human fibroblasts were cultured in a 12-well plate at a concentration of $10^5$ cells/well, and then treated with LPS, after which the medium was replaced with each of media containing 1 ppm, 10 ppm and 100 ppm of the *Chamaecyparis obtusa* polysaccharide. At 2 days of culture, the cells were harvested, and the amount of cyclooxygenase-2 (COX-2) produced in the cells was determined with a densitometer using a Western blot method. The measurement results were calculated relative to 100 for a control group and are shown in Table 9 below.

TABLE 9

| Test material | | COX-2 biosynthesis (%) |
|---|---|---|
| *Chamaecyparis obtusa* polysaccharide | 100 ppm | 31 |
| | 10 ppm | 52 |
| | 1 ppm | 80 |
| Control group | | 100 |

As can be seen from the results in Table 9 above, the *Chamaecyparis obtusa* polysaccharide of the present invention concentration-dependently reduced the biosynthesis of cyclooxygenase-2 induced by the inflammatory response inducer LPS, thereby inhibiting inflammatory responses. Thus, the *Chamaecyparis obtusa* polysaccharide has also an excellent effect of effectively inhibiting skin inflammatory responses to relieve skin troubles.

Experimental Example 11

Test for Inflammation Inhibitory Effect (Mouse Model)

The tetradecanoyl phorbol acetate (TPA)-induced mouse ear inflammation model is an experimental method which is widely used to test the mechanism of action of inflammatory responses and the effect of inhibitors (De Young L M et al., *Agents and Actions*, 26; 335-341 (1989)).

In order to confirm the inflammation inhibitory effect of the *Chamaecyparis obtusa* polysaccharide, 8-week-old male ICR mice (8 animals per group) were prepared. The test group was treated with TPA and applied with a solution of the *Chamaecyparis obtusa* polysaccharide dispersed in a 80% ethanol aqueous solution, the untreated group was applied with a 80% ethanol aqueous solution alone without treatment with TPA, the negative control group was treated with TPA and applied with a 80% ethanol aqueous solution alone, and the positive control group was treated with TPA and applied with 0.5 mg of indomethacine (Sigma, USA) in place of the *Chamaecyparis obtusa* polysaccharide.

The *Chamaecyparis obtusa* polysaccharide obtained in Preparation Example 1 was dispersed in a 80% ethanol aqueous solution at a concentration of 0.5%, after which the ear portion of the test mice was pretreated with the dispersion twice a day for 2 days before application of TPA, and the dispersion was applied again 30 minutes after application of TPA. 2.5 μl of a solution of 2.5 μg/Ml of TPA (Sigma, USA) in acetone was applied to the left ear to induce skin irritation. The mice of the untreated group, the negative control group and the positive control group were also treated as described above. At 24 hours after application of TPA, the mice were euthanized by cervical dislocation, and the left ear was sampled in a given area, and the weight thereof was measured. When the ear is treated with TPA alone, the ear weight is increased due to the occurrence of inflammation, but when the ear is applied with TPA together with the test substance, the ear weight is reduced, and the reduction in the ear weight is referred to as inhibition(%).

The inhibition (%) is calculated according to the following equation 4. The results of the calculation are shown in Table 10 below.

Inhibition (%)=ear weight of group treated with TPA alone−ear weight of untreated group)/(ear weight of group treated with TPA alone−ear weight after treatment with test substance)×100    [Equation 4]

TABLE 10

| | Ear weight (mean ± SD) | Inhibition (%) (mean) |
|---|---|---|
| Untreated group | 6.64 ± 0.65 | — |
| Group treated with TPA alone | 13.21 ± 2.49 | — |
| Indomethacin (0.5 mg/ear) | 7.20 ± 0.57 | 92 |
| *Chamaecyparis obtusa* polysaccharide | 8.63 ± 1.10 | 70 |

As can be seen in Table 10 above, the test group treated with the *Chamaecyparis obtusa* polysaccharide significantly inhibited the TPA-induced inflammatory responses compared with the group treated with TPA alone. This suggests that the *Chamaecyparis obtusa* polysaccharide of the present invention shows an excellent anti-inflammatory effect when it is applied to the skin.

Experimental Example 12

Test for Inhibition of Skin Irritation (Rabbit Model)

Retinoic acid is widely used in cosmetics and medical drugs due to various excellent effects, including promotion of differentiation of the skin's horny layer, treatment of acne, reduction of skin wrinkles, and the like (Fisher et al., *J. Investig. Dermatol.*, 3: 61-68 (1998)). However, it was reported that, when retinoic acid is locally applied to the skin, it causes skin irritation at the initial state and further causes side effects such as skin erythema and edema (Varani et al., *Arch. Dermatol. Res.*, 295: 255-262 (2003)). Accordingly, attempts to reduce this skin irritation of retinoic acid have been made in various ways (Kim et al., *Toxicol. Letters.*, 146: 65-73 (2003)). Meanwhile, New Zealand white rabbits show high responses to various skin irritating substances and have a small difference between individuals, and thus are widely used in skin irritation tests. Thus, in this experiment, skin irritation in New Zealand white rabbits was induced by retinoic acid, after which the degree of a reduction in skin irritation by the test substance was evaluated.

One day before initiation of the experiment, the hair of the back of four New Zealand white rabbits (each weighing 2.0-2.5 kg) was shaved. The shaved back of each rabbit was marked with four application portions (which are symmetric for two; right upper portion-left upper portion, and right lower portion-left lower portion). Also, each of retinoic acid (0.025%) and the *Chamaecyparis obtusa* polysaccharide (0.5%) obtained in Preparation Example 1 was dissolved in a mixed solution of PEG400 and ethanol (7/3 v/v) to prepare test solutions.

100 μl of 0.025% retinoic acid solution (Sigma, USA) was locally applied to all the four application portions of the rabbit back. 30 minutes after application, one portion of the symmetric application portions was treated with the *Chamaecyparis obtusa* polysaccharide solution (100 μl/application portion), and the other portion was treated with the mixed solution (100 μl/application portion) alone. Each of the test solutions was locally applied twice every day for 4 days, and at 5 days of application, the application portions were visually observed to determine the degree of skin irritation, and the skin irritation in each test group was indicated as a cumulative irritation index.

The cumulative irritation index was rated by a five-point scale: 0: no erythema; 1: visible weak erythema; 2: clear erythema; 3: red strong erythema; and 4: deep red strong erythema and crust formation.

Also, a reduction in the cumulative irritation index of the test group treated with both retinoic acid and the acidic polysaccharide solution, relative to the cumulative irritation index of the control group treated with the retinoic acid solution alone, was calculated to determine inhibition (%) as the index of the skin irritation inhibitory effect. The results of the measurement are shown in Table 11 below.

TABLE 11

| Test material | Cumulative irritation index (mean ± SD) | Inhibition (%) (mean) |
|---|---|---|
| Retinoic acid (control group) | 3.23 ± 0.46 | 0% |
| Retinoic acid + *Chamaecyparis obtusa* polysaccharide | 2.34 ± 0.35 | 27.6% |

As can be seen in Table 11 above, the test group treated with the *Chamaecyparis obtusa* polysaccharide showed a reduction in cumulative irritation index of about 27.7% compared to the test group treated with retinoic acid alone. This suggests that the *Chamaecyparis obtusa* polysaccharide of the present invention has an excellent effect on the inhibition of skin irritation.

Experimental Example 13

Measurement of Wound Healing by In Vitro Wound Healing Assay

The human keratinocyte HaCaT cell line used in this Example was obtained from the Korean Cell Line Bank (Seoul, Korea). The HaCaT cells were added to a DMEM medium containing 10% (v/v) FBS, 100 U/Ml of penicillin and 100 μg/Ml of streptomycin and cultured in an animal cell incubator under conditions of 37° C. and 5% $CO_2$. The HaCaT cells prepared at concentration of $1.5 \times 10^6$ cells/well were cultured for 24 hours to form a HaCaT cell monolayer which was then scratched with a p200 pipetter tip. The scratched cell layer was cultured for 24 hours in a medium treated with 10 ppm of the *Chamaecyparis obtusa* polysaccharide obtained in Preparation Example 1, and a negative control group was treated with the same amount of DMSO (dimethyl sulfoxide) which was used to dissolve the *Chamaecyparis obtusa* polysaccharide. The degree of repair of the scratch wound was observed with a microscope equipped with a micro-image video camera (Boyertown, Pa.). The results of the observation are shown in FIG. 1.

Figure 1:
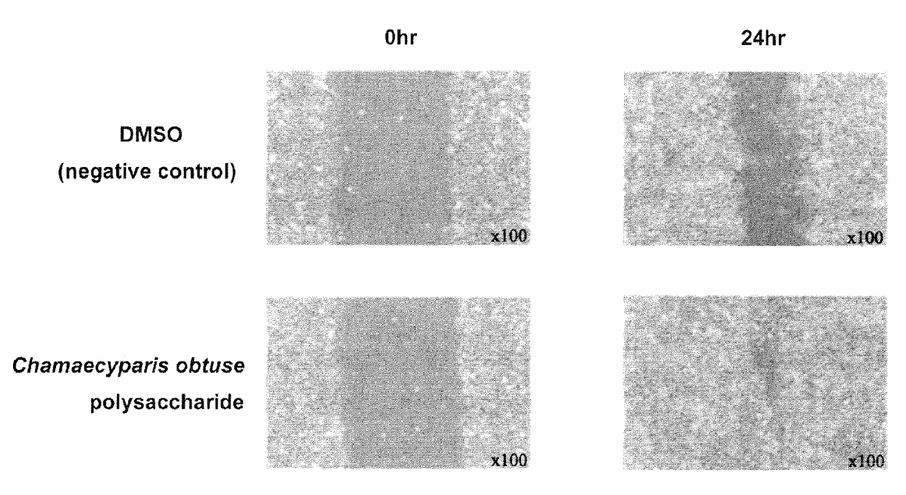
FIG. 1 is a set of photographs showing wound healing effects measured before and after application of a *Chamaecyparis obtusa* polysaccharide using an in vitro wound healing assay.

As can be seen from the results in FIG. 1, the scratch wound of the cells treated with the negative control group remained unhealed after 24 hours, whereas the scratch wound of the cells treated with the *Chamaecyparis obtusa* polysaccharide was healed due to the proliferation and migration of the cells of the wound edge, and the scratch area was substantially restored after 24 hours. This suggests that the *Chamaecyparis obtusa* polysaccharide of the present invention has excellent effects on skin wound healing and skin regeneration.

Hereinafter, formulation examples of the composition according to the present invention will be described, but the scope of the present invention is not limited thereto.

Formulation Example 1

Skin Lotion

TABLE 12

| Components | Contents (wt %) |
|---|---|
| Purified water | Balance |
| *Chamaecyparis obtusa* polysaccharide | 0.1 |
| Butylene glycol | 2.0 |
| Propylene glycol | 2.0 |
| Carboxyvinyl polymer | 0.1 |
| PEG-12 nonylphenylether | 0.2 |
| Polysorbate 80 | 0.4 |
| Ethanol | 10.0 |
| Triethanolamine | 0.1 |
| Preservative, pigment and fragrance | q.s. |

Formulation Example 2

Milk Lotion

TABLE 13

| Components | Contents (wt %) |
|---|---|
| Purified water | Balance |
| *Chamaecyparis obtusa* polysaccharide | 0.1 |
| Beeswax | 4.0 |
| Polysorbate 60 | 1.5 |
| Sorbitan sesquioleate | 1.5 |
| Liquid paraffin | 0.5 |
| Montana 202 (manufactured by Seppic) | 5.0 |
| Glycerin | 3.0 |
| Butylene glycol | 3.0 |
| Propylene glycol | 3.0 |
| Carboxyvinyl polymer | 0.1 |

Formulation Example 3

Massage Cream

TABLE 14

| Components | Content (wt %) |
|---|---|
| Purified water | Balance |
| *Chamaecyparis obtusa* polysaccharide | 0.1 |
| Beeswax | 10.0 |
| Polysorbate 60 | 1.5 |
| PEG 60 hydrogenated castor oil | 2.0 |
| Sorbitan sesquioleate | 0.8 |
| Liquid paraffin | 40.0 |
| Squalane | 5.0 |
| Montana 202 (manufactured by Seppic) | 4.0 |
| Glycerin | 5.0 |
| Butylene glycol | 3.0 |
| Propylene glycol | 3.0 |
| Triethanolamine | 0.2 |
| Preservative, pigment and fragrance | q.s. |

Formulation Example 4

Pack

TABLE 4

| Components | Contents (wt %) |
|---|---|
| Purified water | Balance |
| *Chamaecyparis obtusa* polysaccharide | 0.1 |
| Polyvinyl alcohol | 13.0 |
| Sodium carboxymethylcellulose | 0.2 |
| Glycerin | 5.0 |
| Allantoin | 0.1 |
| Ethanol | 6.0 |
| PEG-12 nonylphenylether | 0.3 |

TABLE 4-continued

| Components | Contents (wt %) |
|---|---|
| Polysorbate 60 | 0.3 |
| Preservative, pigment and fragrance | q.s. |

The invention claimed is:

1. A composition for skin external application containing a *Chamaecyparis obtuse* polysaccharide extract having a molecular weight of at least 100,000 Daltons, devoid of (i) chlorophyll and (ii)) proteins having a molecular weight of below 1,000 Da.

2. The composition of claim 1, wherein the *Chamaecyparis obtuse* polysaccharide extract is present in an amount of 0.001-10 wt % based on the total weight of the composition.

3. The composition of claim 1, wherein the composition is for anti-aging.

4. The composition of claim 1, wherein the composition is for reducing skin wrinkles.

5. The composition of claim 1, wherein the composition is for improving skin elasticity.

6. The composition of claim 1, wherein the composition is for skin whitening.

7. The composition of claim 1, wherein the composition is for skin moisturization.

8. The composition of claim 1, wherein the composition is for amelioration of dry skin diseases.

9. The composition of claim 1, wherein the composition is for anti-inflammation.

10. The composition of claim 1, wherein the composition is for promoting skin regeneration.

11. The composition of claim 1, wherein the *Chamaecyparis obtuse* polysaccharide extract is prepared by:
   a) removing chlorophyll from dried *Chamaecyparis obtusa* leaves using a solvent;
   b) hot-water extracting water-soluble active ingredients from the leaf residue of step a); and
   c) separating the polysaccharides of *Chamaecyparis obtusa* from the hot-water extract of step b) by ultra-filtration and ethanol precipitation.

12. A method of combating aging, reducing skin wrinkles, improving skin elasticity, skin whitening, skin moisturization, ameliorating dry skin diseases, treating inflammation, or promoting skin regeneration comprising transdermally applying to a subject in need of an effective amount of a *Chamaecyparis obtuse* polysaccharide extract having a molecular weight of at least 100,000 Daltons, devoid of (i) chlorophyll and (ii) proteins having a molecular weight of below 1,000 Da.

* * * * *